United States Patent [19]

Brunelle

[11] Patent Number: 4,595,760

[45] Date of Patent: Jun. 17, 1986

[54] BIS-AMINOPYRIDINIUM SALTS

[75] Inventor: Daniel J. Brunelle, Scotia, N.Y.

[73] Assignee: General Electric Company, Schenectady, N.Y.

[21] Appl. No.: 553,713

[22] Filed: Nov. 21, 1983

[51] Int. Cl.$^4$ .................. C07D 401/06; C07D 401/04
[52] U.S. Cl. ..................... 546/256; 546/264; 546/187
[58] Field of Search ............. 546/256, 264, 187

[56] References Cited

U.S. PATENT DOCUMENTS

| | | | |
|---|---|---|---|
| 3,458,305 | 7/1969 | Doyle | 546/256 |
| 4,107,313 | 8/1978 | Bailey | 546/264 |
| 4,206,215 | 6/1980 | Bailey | 546/264 |
| 4,256,458 | 3/1981 | Degen et al. | 546/256 |
| 4,273,712 | 6/1981 | Williams, III | 548/461 |
| 4,460,778 | 7/1984 | Brunelle | 546/304 |

FOREIGN PATENT DOCUMENTS 0702535  1/1965  Canada .................. 546/256

Primary Examiner—Jane T. Fan
Attorney, Agent, or Firm—William H. Pittman; James C. Davis, Jr.; James Magee, Jr.

[57] ABSTRACT

Novel bis-aminopyridinium salts are useful as phase transfer catalysts in the preparation of aromatic ethers by the reaction of hydroxyaromatic compound alkali metal salts (e.g., bisphenol A disodium salt) with activated halo- or nitro-substituted aromatic compounds (e.g., 4-nitro-N-methylphthalimide). The bis-aminopyridinium salts may be prepared by the reaction of aminopyridines with bis-carbonium ion-generating compounds such as dibromoalkanes.

12 Claims, 1 Drawing Figure

(I) 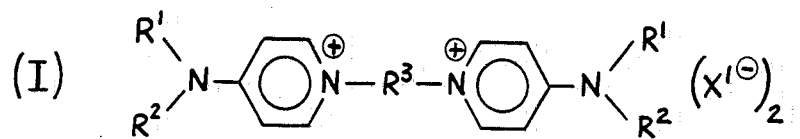
(II) 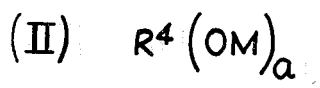
(III) 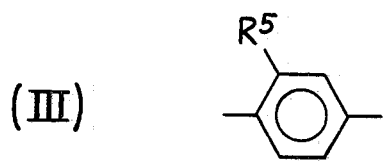
(IV) 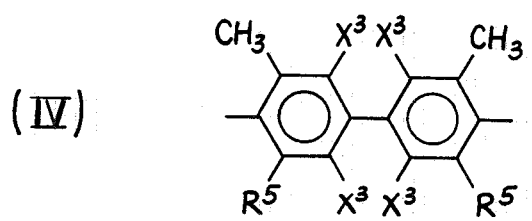
(V) 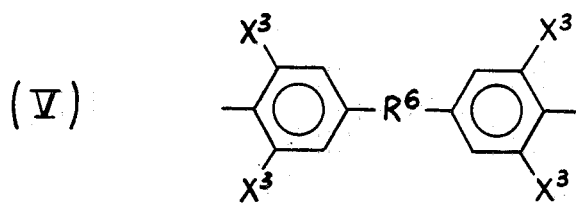
(VI) 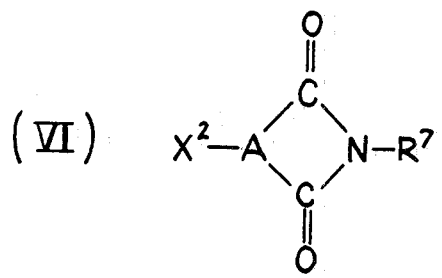

BIS-AMINOPYRIDINIUM SALTS

This invention relates to new compositions of matter useful in the preparation of aromatic ether imides, and more particularly to their use as improved phase transfer catalysts for use in said preparation.

Aromatic ether imides are a known class of compounds. It is also known that various aromatic ether bisimides such as 2,2-bis[4-(3,4-dicarboxyphenoxy)phenyl] propane bis-N-methylimide may be converted to dianhydrides, which in turn may be reacted with diamines to produce polyetherimides. Certain bisimides can also be reacted directly with diamines to produce polyetherimides, as disclosed and claimed in copending, commonly assigned application Ser. No. 505,636, filed June 20, 1983. The analogous monoimides and corresponding monoanhydrides can be used, for example, as end-capping or chain-stopping agents for polyetherimides.

A convenient method of preparing aromatic ether imides and similar compounds is by the nucleophilic displacement reaction of a substituted aromatic compound, most often an imide such as a substituted phthalimide, wherein the substituents may be, for example, halo or nitro, with an alkali metal salt of a hydroxyaromatic compound. This reaction is often conveniently effected in solution in a substantially non-polar organic solvent, in the presence of a phase transfer catalyst. U.S. Pat. No. 4,273,712 describes suitable reaction conditions and the use of various quaternary ammonium and phosphonium salts as phase transfer catalysts. The use of aminopyridinium salts for the same purpose is disclosed in applications Serial No. 489,689 and 489,690 (now U.S. Pat. No. 4,460,778), both filed Apr. 28, 1983, and the use of bis-quaternary ammonium salts in application Ser. No. 542,242, filed Oct. 14, 1983. All of said applications are copending and commonly assigned herewith, and the disclosures thereof and of said patents are incorporated by reference herein.

It is frequently found that a relatively large amount of quaternary ammonium or phosphonium salt must be used as a phase transfer catalyst in the displacement reaction, in order for it to proceed rapidly enough to produce the ether imide in an economically feasible time period. It is of interest, therefore, to develop phase transfer catalysts which can be used in smaller proportions.

A principal object of the present invention, therefore, is to provide novel bis-aminopyridinium salts.

A further object is to provide novel compounds useful as phase transfer catalysts.

A further object is to provide phase transfer catalysts which can be used in very small quantities.

Still another object is to provide an improved method for the preparation of aromatic ether imides by the reaction of substituted aromatic imides with alkali metal phenoxides.

Other objects will in part be obvious and will in part appear hereinafter.

In its broadest sense, the present invention includes novel bis-aminopyridinium salts having formula I in the drawings, wherein:

each of $R^1$ and $R^2$ is independently an aliphatic hydrocarbon-based radical containing about 1–13 carbon atoms, or $R^1$ and $R^2$ together form a divalent aliphatic hydrocarbon-based radical containing about 4–13 carbon atoms;

$R^3$ is a divalent hydrocarbon-based radical containing about 4–25 atoms in a single chain connecting the quaternary nitrogen atoms; and $X^1$ is an anion-forming atom or radical.

The term "hydrocarbon-based radical" as used herein denotes a radical free from acetylenic and usually also from ethylenic unsaturation, having a carbon atom directly attached to the remainder of the molecule and having predominantly hydrocarbon character within the context of this invention. Such radicals include the following:

(1) Hydrocarbon radicals, which may be aliphatic (e.g., methyl, n-propyl, isopropyl, n-butyl, 1-pentyl, 2-pentyl, 1-hexyl, oleyl), aromatic (e.g., phenyl, p-tolyl, 1-naphthyl, 2-naphthyl), alicyclic (e.g., cyclopentyl, cyclohexyl), aromatic- or alicyclic-substituted aliphatic, aliphatic-substituted aromatic, or the like.

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., nitro, hydroxy, alkoxy, carbalkoxy).

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

The $R^1$ and $R^2$ values in the compounds of this invention may be as previously noted, aliphatic hydrocarbon-based (preferably hydrocarbon and usually alkyl) radicals containing about 1–13 and most often 1–8 carbon atoms, and $R^1$ and $R^2$ are then usually identical. Alternatively, $R^1$ and $R^2$ together may form a divalent aliphatic hydrocarbon-based, preferably hydrocarbon and usually alkylene radical containing about 4–13 carbon atoms such as tetramethylene, pentamethylene or alkyl-substituted derivatives thereof; in other words, $R^1$, $R^2$ and the nitrogen atom linking them form a heterocyclic radical such as piperidyl (especially) or pyrrolidyl.

The $R^3$ value is a divalent hydrocarbon-based radical; it may be an aliphatic (usually alkylene), alicyclic (usually cycloalkylene) or aromatic radical such as tetramethylene, hexamethylene, octamethylene, decamethylene, dodecamethylene, cyclohexylene, phenylene, tolylene or naphthylene. It may also be a hetero radical, as exemplified by heterocyclic radicals derived from compounds such as pyridine and indole, or more often, linear hetero radicals in which the hetero atoms are oxygen; examples of such radicals are those derived from polyethylene glycol and polypropylene glycol. Preferably, $R^3$ is alkylene, especially straight chain alkylene, or poly(oxyethylene).

The $R^3$ radical contains about 4–25, preferably about 5–15 and most desirably 6–12, atoms in a single chain connecting the quaternary nitrogen atoms in formula I. For maximum solubility in the displacement reaction mixture, the particularly preferred compounds of formula I are those in which the total of carbon atoms in all $R^{1-3}$ radicals and other chain atoms in $R^3$, if any, is at least 15 and especially at least 30.

The $X^1$ value may be any anion which is stable under the conditions of the displacement reaction; suitable anions include chloride, bromide, sulfate, p-toluenesulfonate and methanesulfonate. Because of the ready availability and particular suitability of bromide and methanesulfonate reagents for the preparation of the bis-aminopyridinium salts, $X^1$ is usually one of these anions.

The bis-aminopyridinium salts of this invention may be prepared by the reaction of a suitable aminopyridine such as 4-dimethylaminopyridine, 4-di-n-hexylaminopyridine or 4-(4-methyl-1-piperidinyl)pyridine with a bis-carbonium ion-generating compound, typically an alkylene or polyoxyalkylene dichloride, dibromide, bis-methanesulfonate or the like. The stoichiometry of the reaction requires about 2 moles of aminopyridine per mole of bis-carbonium ion-generating compound. Suitable reaction temperatures are generally about 50°–125° C. It is sometimes advantageous to effect the reaction in a substantially inert organic diluent such as benzene, toluene, acetonitrile, petroleum naphtha or the like. The products may be isolated by known methods, typically by precipitation with a non-solvent, filtration and/or drying in the case of solid products.

The preparation of the bis-aminopyridinium salts of this invention is illustrated by the following examples. All parts are by weight. Structures were proved correct by nuclear magnetic resonance spectra.

EXAMPLE 1

Tetraethylene glycol bis-methanesulfonate was prepared by the reaction of 1.94 parts (10.0 mmol.) of tetraethylene glycol, 2.31 parts (20.2 mmol.) of methanesulfonyl chloride and 2.04 parts (20.2 mmol.) of triethylamine. There was then added 2.04 parts (20.0 mmol.) of dimethylaminopyridine and the mixture was heated at 100° C. for 2 hours. The product was the desired tetraethylene glycol bis-(4-dimethylaminopyridinium) bis-methanesulfonate the compound of formula I wherein $R^1$ and $R^2$ are each methyl, $R^3$ is $C_2H_4(OC_2H_4)_3$ and $X^1$ is $CH_3SO_3$.

EXAMPLE 2

A solution in toluene of 2.442 parts (0.02 mole) of 4-dimethylaminopyridine and 2.72 parts (0.01 mole) of 1,8-dibromooctane was heated at 75° C. for 1 hour. The product, the desired 1,8-bis(4-dimethylaminopyridinium)octane dibromide, precipitated and was separated by filtration and dried.

EXAMPLE 3

Following the procedure of Example 2, 1,10-bis(4-dimethylaminopyridinium)decane dibromide was obtained by the reaction of 2.442 parts (0.02 mole) of 4-dimethylaminopyridine with 3 parts (0.01 mole) of 1,10-dibromodecane.

EXAMPLE 4

A solution in toluene of 2.624 parts (10 mmol.) of 4-di-n-hexylaminopyridine and 1.22 parts (5 mmol.) of 1,6-dibromohexane was heated at 75° C. for 24 hours. The product, 1,6-bis(4-di-n-hexylaminopyridinium)hexane dibromide, precipitated and was removed by filtration and dried.

EXAMPLE 5–6

Following the procedure of Example 4, 10 mmol. of 4-di-n-hexylaminopyridine was reacted with 5 mmol. of 1,8-dibromooctane and 1,10-dibromodecane, respectively. The products were the desired bis-aminopyridinium dibromides.

EXAMPLE 7

An acetonitrile solution of 3.52 parts (0.02 mole) of 4-(4-methyl-1-piperidinyl)pyridine and 3 parts (0.01 mole) of 1,10-dibromodecane was heated at 75° C. for 2 hours. Upon cooling and addition of toluene, the product, the desired 1,10-bis[4-(4-methyl-1-piperidinylpyridinium)decane]dibromide precipitated; it was removed by filtration and dried in vacuum.

As previously mentioned, the bis-aminopyridinium salts of this invention are useful as phase transfer catalysts in nucleophilic displacement reactions. Accordingly, another embodiment of the invention is an improvement in a method for preparing an aromatic ether by the reaction, in a non-polar organic solvent in the presence of a phase transfer catalyst, of (A) at least one hydroxyaromatic compound alkali metal salt having the formula II
wherein $R^4$ is an aromatic radical containing about 6–30 carbon atoms, M is an alkali metal and a is 1 or 2, with (B) at least one activated halo- or nitro-substituted aromatic compound; said improvement comprising using as said phase transfer catalyst at least one such bis-aminopyridinium salt.

Reagent A in the method of this invention is at least one alkali metal salt of a mono- or dihydroxyaromatic compound, depending on whether a is 1 or 2. The M value may be any alkali metal; it is usually lithium, sodium or potassium and preferably sodium.

The $R^4$ value may be any aromatic radical containing about 6–30 carbon atoms. It may be a hydrocarbon radical or may contain other atoms such as oxygen or sulfur. Illustrative monovalent radicals (i.e., those derived from compounds in which a is 1) include phenyl, m-tolyl, p-tolyl, 1-naphthyl, 2-naphthyl, p-chlorophenyl and 4-bromo-1-naphthyl.

Most often, $R^4$ is a divalent aromatic radical; i.e., a is 2. Illustrative radicals of this type are derived from such compounds as resorcinol, hydroquinone,
4,4′-dihydroxybiphenyl,
4,4′-dihydroxy-3,3′,5,5′-tetramethylbiphenyl,
4,4′-dihydroxydiphenylmethane, 3,4′-dihydroxydiphenylmethane, 2,2-bis(2-hyroxyphenyl)propane,
2,2-bis(4-hydroxyphenyl)-propane (hereinafter "bisphenol A")
2-(3-hydroxyphenyl)-2-(4-hydroxyphenyl) propane, 1,1-bis-(4-hydroxyphenyl)ethane, 2,2-bis(4-hydroxyphenyl)pentane,
4,4′-dihydroxybenzophenone,
bis(4-hydroxyphenyl) ether, bis(4-hydroxyphenyl sulfide,
bis(4-hydroxyphenyl) sulfoxide, bis(4-hydroxyphenyl) sulfone and 3-hydroxphenyl 4-hydroxyphenyl sulfone.

The radicals preferred as $R^1$ have formulas III, IV and V,
wherein $R^5$ is independently hydrogen or methyl, $R^6$ is a straight-chain or branched alkylene radical containing 1–5 carbon atoms and is most often the isopropylidene radical, and each $X^3$ is independently hydrogen or halogen (usually chlorine or bromine). Mixtures of the foregoing formulas are also contemplated. Especially desirable is the radical derived from bisphenol A by the removal of both hydroxy groups therefrom, and having formula V wherein $R^6$ is isopropylidene and each $X^3$ is hydrogen.

Reagent B is at least one activated halo- (usually fluoro- or chloro-) or (preferably) nitro-substituted aromatic compound. By "activated" in the context of this invention is meant a compound having an electron-deficient aromatic ring. Electron deficiency may be achieved by the presence of electron-withdrawing substituents such as halo, nitro, keto, cyano, carboxy, carbalkoxy, perfluoroalkyl or the like, or by the presence of hetero atoms such as nitrogen (e.g., as part of a pyridine ring).

Most often, reagent B is at least one substituted imide having the formula VI, wherein A is an aromatic radical, $R^7$ is hydrogen or a hydrocarbon-based radical containing about 1–13 carbon atoms and $X^2$ is halo or nitro. The A value may be an aromatic radical which contains about 6–30 carbon atoms and which is capable of forming an imide. In general, these are radicals derived from o-dicarboxylic acids such as phthalic acid and 2,3-naphthalenedicarboxylic acid; however, radicals derived from acids such as 1,8-naphthalenedicarboxylic acid are also suitable. Most preferably, A is derived from phthalic acid; i.e., it is the o-phenylene radical.

The $R^7$ value is hydrogen or a hydrocarbon-based radical containing from 1 to about 13 carbon atoms. A preferred subgenus of $R^7$ radicals consists of alkyl and especially lower alkyl radicals, the term "lower" denoting not more than 7 carbon atoms. The preferred lower alkyl radical is methyl.

A second preferred subgenus of $R^7$ radicals consists of electron-deficient radicals. For the most part, these comprise aromatic hydrocarbon radicals containing one or more strongly electron-withdrawing substituents such as those previously listed with reference to A, and heterocyclic radicals having aromatic character. Compounds in which $R^7$ is of this type are disclosed and claimed in the aforementioned application Ser. No. 505,636, the disclosure of which is incorporated by reference herein.

Suitable aromatic hydrocarbon radicals include phenyl, naphthyl and the like containing electron-withdrawing substituents of which at least one is preferably ortho or para to the free valence bond (i.e., the one attached to the imide nitrogen atom). The trifluoromethylphenyl radicals are particularly preferred.

Suitable heterocyclic radicals having aromatic character include those with 5-or 6-membered rings and aromatic unsaturation of the type existing in pyrrole and pyridine. These radicals preferably contain 1–3 and especially 1 or 2 hetero atoms of which at least one is nitrogen and the others, if present, are nitrogen or sulfur. They are usually unsubstituted but may be substituted, especially with electron-withdrawing substituents such as those previously enumerated. The free valence bond is preferably in the 2- or 4-position with respect to a hetero atoms. If the ring contains more than one hetero atom, and especially if it is 5-membered, the free valence bond is preferably attached to the single carbon atom between two of said hetero atoms.

Illustrative 5-membered heterocyclic radicals are pyrrolyl, 2-thiazolyl, 2-imidazolyl and 2-(1,3,4-thiadiazolyl). Illustrative 6-membered radicals are 2-pyridyl, 3-pyridyl, 4-pyridyl, 2-pyrimidyl, 2-pyrazyl, 2-(1,4,-thiazolyl) and 2-(1,3-thiazolyl). Particularly preferred heterocyclic radicals are the aminopyridyl radicals, especially 2-pyridyl and 4-pyridyl.

According to the present invention, the reaction between reagents A and B is ordinarily effected at a temperature within the range of about 25°–150° C., preferably about 100°–120° C., in a non-polar organic solvent such as benzene, toluene, xylene, chlorobenzene, o-dichlorobenzene, tetrahydrofuran, acetonitrile, octane or the like. It is preferred to use approximately equivalent amounts of the two reagents, which includes the use of a slight excess (usually no more than about 5 mole percent) of either.

The bis-aminopyridinium salt is usually present in the reaction mixture in the amount of about 0.001–2.0 equivalents per equivalent of reagent A. (For the purposes of this invention, the equivalent weight of reagent A is its molecular weight divided by the number of aromatic hydroxy groups present therein, and that of the bis-aminopyridinium salt is half its molecular weight.) It is seldom necessary, however, to use more than about 0.2 equivalent of phase transfer catalyst per equivalent of reagent A. Since a characteristic of the present invention is that the bis-aminopyridinium salt may be used in very small amounts, the preferred concentration range thereof is about 0.002–0.04 equivalent per equivalent of reagent A.

The method of this invention is illustrated by the following examples.

EXAMPLE 8

As solution in toluene of 0.28 part (1 mmol.) of bisphenol A disodium salt, 0.28 part (2 mmol.) of 4-fluoronitrobenzene, 0.025 part of m-terphenyl (used as an internal standard) and 0.00475 part (0.008 mmol.) of the product of Example 1 was heated under reflux for 2 hours. Analysis of the reaction mixture by high pressure liquid-liquid chromatography showed a quantative yield of the desired 2,2-bis(4-nitrophenoxyphenyl)propane.

EXAMPLE 9

Various amounts of the bis-aminopyridinium salts of this invention were added as phase transfer catalysts to a toluene solution of 0.56 part (2 mmol.) of bisphenol A disodium salt, 0.824 part (4 mmol.) of 4-nitro-N-methylphthalimide and 0.05 part of m-terphenyl (used as an internal standard). The mixtures were heated to reflux and sampled periodically, with the progress of the reaction and the yield of 2,2-bis[4-(3,4-dicarboxyphenoxy)phenyl]propane bis-N-methylimide being followed by high pressure liquid-liquid chromatography. The results are listed in the following table.

| Bis-amino-pyridinium salt of Example | Equivs. per equiv. of Bisphenol A salt | Time, hrs. | Yield of bisimide, % |
| --- | --- | --- | --- |
| 4 | 0.0075 | 0.5 | 92 |
|   |        | 1.0 | 97 |
|   |        | 2.0 | 100 |
|   | 0.005  | 0.5 | 76 |
|   |        | 1.0 | 93 |
|   |        | 2.0 | 100 |
|   | 0.0025 | 0.5 | 47 |
|   |        | 1.0 | 63 |
|   |        | 2.0 | 94 |
|   |        | 4.0 | 96 |
| 7 | 0.02   | 0.5 | 20 |
|   |        | 1.0 | 59 |
|   |        | 2.0 | 88 |
|   |        | 4.0 | 98 |
|   | 0.01   | 0.5 | 14 |

| Bis-amino-pyridinium salt of Example | Equivs. per equiv. of Bisphenol A salt | Time, hrs. | Yield of bisimide, % |
| --- | --- | --- | --- |
| | | 1.0 | 44 |
| | | 2.0 | 79 |
| | | 4.0 | 95 |
| | 0.007 | 0.5 | 11 |
| | | 1.0 | 33 |
| | | 2.0 | 66 |
| | | 4.0 | 87 |

The results in the table show the effectiveness of the bis-aminopyridinium salts of this invention as phase transfer catalysts.

What is claimed is:

1. A bis-aminopyridinium salt having the formula

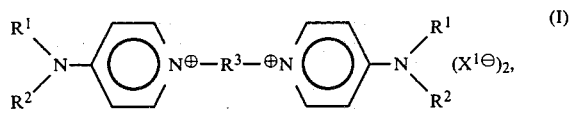 (I)

wherein:

R$^1$ and R$^2$ are identical alkyl radicals containing 1–13 carbon atoms or R$^1$ and R$^2$ together form a tetramethylene, pentamethylene or alkyl-substituted tetramethylene or pentamethylene radical;

R$^3$ is an alkylene or poly(oxyethylene) radical containing 4–25 atoms in a single chain connecting the quaternary nitrogen atoms; and X$^1$ is an anion-forming atom or radical.

2. A salt according to claim 1 wherein R$^3$ contains 5–15 atoms in said chain.

3. A salt according to claim 2 wherein the total of carbon and oxygen atoms in all R$^{1-3}$ radicals is at least 15.

4. A salt according to claim 3 wherein each of R$^1$ and R$^2$ is an alkyl radical containing 1–8 carbon atoms.

5. A salt according to claim 4 wherein R$^3$ is a straight chain alkylene radical containing 6–12 carbon atoms.

6. A salt according to claim 5 wherein X$^1$ is bromide or methanesulfonate.

7. A salt according to claim 6 wherein each of R$^1$ and R$^2$ is methyl.

8. A salt according to claim 6 wherein each of R$^1$ and R$^2$ is n-hexyl.

9. A salt according to claim 3 wherein R$^1$ and R$^2$ together form a tetramethylene or pentamethylene radical or alkyl-substituted derivative thereof.

10. A salt according to claim 9 wherein R$^1$, R$^2$ and the nitrogen atom linking them form a 4-methylpiperidyl radical.

11. A salt according to claim 10 wherein R$^3$ is a straight chain alkylene radical containing 6–12 carbon atoms.

12. A salt according to claim 11 wherein X$^1$ is bromide or methanesulfonate.

* * * * *